(12) United States Patent
Orr et al.

(10) Patent No.: US 6,475,158 B1
(45) Date of Patent: Nov. 5, 2002

(54) CALORIMETRY SYSTEMS AND METHODS

(75) Inventors: Joseph A. Orr, Park City; Scott A. Kofoed, Bountiful; Kevin Durst, Salt Lake City, all of UT (US)

(73) Assignee: Korr Medical Technologies, Inc., Salt Lake City, UT (US)

(*) Notice: Subject to any disclaimer, the term of this patent is extended or adjusted under 35 U.S.C. 154(b) by 62 days.

(21) Appl. No.: 09/694,954

(22) Filed: Oct. 24, 2000

(51) Int. Cl.⁷ .................................................. A61B 5/08
(52) U.S. Cl. ...................... 600/531; 600/529; 600/532
(58) Field of Search .............................. 600/529–538

(56) References Cited

U.S. PATENT DOCUMENTS

| | | | |
|---|---|---|---|
| 4,457,310 A | * 7/1984 | Swyer et al. | 600/481 |
| 4,572,208 A | 2/1986 | Cutler et al. | |
| 4,619,269 A | * 10/1986 | Cutler et al. | 128/204.16 |
| 4,658,832 A | * 4/1987 | Brugnoli | 340/870.09 |
| 4,856,531 A | 8/1989 | Meriläinen | |
| 4,909,259 A | * 3/1990 | Tehrani | 600/483 |
| 5,046,502 A | * 9/1991 | Kunig | 600/481 |
| 5,285,794 A | * 2/1994 | Lynch | 600/532 |
| 5,357,971 A | * 10/1994 | Sheehan et al. | 128/205.12 |
| 5,363,857 A | * 11/1994 | Howard | 600/531 |
| 5,404,885 A | * 4/1995 | Sheehan et al. | 128/204.22 |
| 6,013,009 A | 1/2000 | Karkanen | |
| 6,174,289 B1 | * 1/2001 | Binder | 422/83 |
| 6,206,837 B1 | * 3/2001 | Brugnoli | 600/529 |
| 6,287,262 B1 | * 9/2001 | Amano et al. | 600/300 |

* cited by examiner

Primary Examiner—Kevin Shaver
Assistant Examiner—Navin Natnithithadha
(74) Attorney, Agent, or Firm—Traskbritt

(57) ABSTRACT

A calorimeter configured to determine a metabolic rate of an individual based on measurements of the individual's respiration. The calorimeter includes an inlet, a flow sensor, a mixing chamber, a gas sensor, and a calibrator. Each of these elements is located along a flow path through the calorimeter. The calibrator of the calorimeter includes a fan that is configured to force calibration gases, such as room air, through or past the gas sensor. A cardiac rate monitor is associated with a processor of the calorimeter. The processor is configured to substantially simultaneously determine and establish a relationship between the cardiac rate of the individual and the measured respiratory parameters or the metabolic rate of the individual. Data representative of this relationship may be communicated to a processor or memory of a portable calorimeter to be subsequently used by the individual. The portable calorimeter, which can be worn by the individual, includes a cardiac rate monitor that measures the cardiac rate of the individual and communicates data representative of the individual's cardiac rate to the processor, which then determines the metabolic rate of the individual based on relationship data obtained from the respiratory-based calorimeter. Methods of calibrating and using the calorimeters are also disclosed.

22 Claims, 2 Drawing Sheets

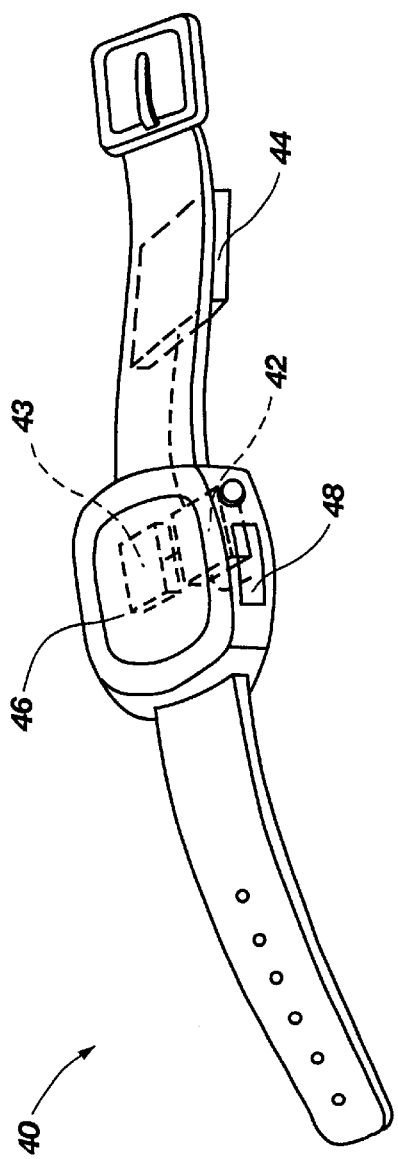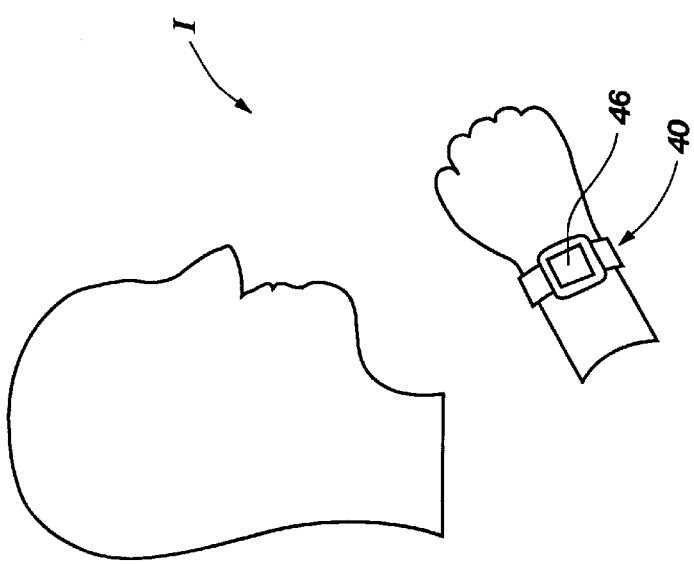

CALORIMETRY SYSTEMS AND METHODS

BACKGROUND OF THE INVENTION

1. Field of the Invention

The present invention relates generally to calorimeters that are configured to evaluate the metabolic rate of an individual based on the individual's respiration. More particularly, the present invention relates to calorimeters that are configured to measure the oxygen consumption of an individual. The present invention also relates to systems that employ measurements taken by calorimeters of the present invention to subsequently determine the cardiac rate of an individual and to therewith evaluate the metabolic rate of an individual, as well as to methods for determining an individual's metabolic rate.

2. Background of Related Art

It is well known that for every calorie of energy generated by the body, a fixed amount of oxygen is consumed. Some conventional calorimetry methods include measurement of the amount of oxygen consumed by an individual to indirectly determine the metabolic rate of the individual, which is the amount of energy, in calories, generated and, thus, the number of calories consumed, or "burned", by the individual over a specific period of time.

Exemplary calorimeters that employ such methods are disclosed in U.S. Pat. No. 4,572,208 to Cutler et al. (hereinafter "Cutler") and U.S. Pat. No. 4,856,531 to Meriläinen (hereinafter "Meriläinen").

Cutler discloses a calorimeter that may be used to determine the metabolic rate of an individual during normal breathing or during respirator-assisted breathing. The Cutler calorimeter includes a mixing chamber for averaging the gases of several expiratory breaths. The flow of the individual's expiratory respiration is measured by a flow sensor that communicates with the mixing chamber. The calorimeter also includes a switching mechanism that controls the flow of inspiratory, expiratory, and calibration gas mixtures therethrough. A cooler reduces or eliminates the presence of water vapor in gases flowing through the calorimeter by causing such water vapor to condense and precipitate from the gases. The calorimeter also includes a carbon dioxide sensor and an oxygen sensor. The oxygen sensor of the calorimeter disclosed in Cutler is calibrated by allowing a calibration gas, such as room air, with known quantities of oxygen and carbon dioxide to flow into a reference chamber through a variable restrictor or valve. The carbon dioxide sensor must be separately calibrated, using at least one different calibration gas mixture. Data representative of the amounts of carbon dioxide and oxygen present in the individual's respiration, as well as data representative of the respiratory flow of the, individual during both inhalation and exhalation, are communicated to a microprocessor, which determines the metabolic rate of the individual. Due to the network of conduits in the Cutler calorimeter, as well as the use of switches and valves therein, a pump is used to draw the calibration or evaluated gas mixtures through and out of the calorimeter.

The calorimeter of Meriläinen is configured to measure the metabolic rate of an individual whose respiration is assisted by a respirator. That calorimeter also includes a mixing chamber within which the gases of multiple expiratory breaths may be averaged. As gases exit the mixing chamber, an air flow moving at a known, fixed flow rate carries the gases through the calorimeter to carbon dioxide and oxygen sensors. Carbon dioxide and oxygen measurements obtained with the sensors and the known flow rate are then used to determine the metabolic rate of the individual. Meriläinen teaches that the carbon dioxide and oxygen sensors of the calorimeter may be calibrated by use of a syringe to inject into the mixing chamber a calibration gas that differs from room air.

Neither the calorimeter disclosed in Cutler nor the calorimeter disclosed in Meriläinen is configured to be used to portably measure the metabolic rate of an individual based on the individual's heart rate.

Another type of calorimeter, which can be used to evaluate the metabolic rate of an individual during exercise, relies on the premise that metabolic rate of each individual is related to that individual's cardiac rate.

In many calorimeters of this type, particularly in calorimeters that are incorporated into exercise equipment and in portable calorimeters that are designed to be worn by an individual, attempts have been made to generalize the relationship between metabolic rate and cardiac rate. Such calorimeters typically require an individual to input information such as age, gender, and weight. This information is used, based on a statistical sampling of a large group of individuals of similar age, gender, and weight, to provide a profile of the individual that is relied upon in estimating the individual's metabolic rate based on cardiac rate measurements. Other factors that may contribute to the metabolic rate of the individual, such as the individual's height, exercise mechanics, cardiac conditioning, and overall physical health, are often not considered when such calorimeters are used to generate metabolic rate data. As a result, these calorimeters are often very inaccurate, providing metabolic rate measurements that vary by as much as 50% or more from the actual metabolic rate of an individual.

U.S. Pat. No. 6,013,009 to Karkanen (hereinafter "Karkanen") discloses a portable heart rate monitor that estimates the metabolic rate of an individual based on measurements of the individual's cardiac rate. The portable heart rate monitor of Karkanen relies upon a personal heart rate curve for the individual in estimating the individual's metabolic rate. In order to generate a personal heart rate curve for an individual, the age and weight of the individual are entered into a microprocessor of the portable heart rate monitor. In addition, data regarding multiple test exercises conducted by the individual, including the type of test exercises conducted by the individual (i.e., running or walking), the speed at which the test exercises were conducted, and the individual's heart rate for each test exercise, are input into the microprocessor of the portable heart rate monitor. For each test exercise, the rate per pound at which the individual burns calories is calculated using a formula that relies upon a statistical sampling of adults that performed the same general type of exercise. The rate per pound is then multiplied by the input weight to determine the rate at which the individual burns calories during each test exercise. Using calorie burn rate data based on each test exercise, a least squares linear regression algorithm is then used to calculate the personal heart rate curve for the individual. During subsequent exercises, this personal heart rate curve is used to estimate, based on the individual's heart rate, the rate at which the individual burns calories or the total amount of calories burned by the individual over a specific time duration.

Because the portable heart rate monitor of Karkanen relies upon a statistical sampling of data to estimate the metabolic rate of an individual, that portable heart rate monitor relies upon averaged data obtained from a large population of people who performed a similar type of exercise. The portable heart rate monitor of Karkanen does not account for unique factors of the individual that may contribute to the individual's metabolic rate.

The inventors are not aware of any portable calorimeters or of any calorimetry systems or methods that employ data representative of an individual's own metabolic rate, as determined based on measurements of the individual's respiration, to subsequently ascertain the metabolic rate of the individual.

SUMMARY OF THE INVENTION

The present invention includes a calorimeter that is configured to evaluate the metabolic rate of an individual by measuring various aspects of the individual's respiration. The calorimeter relates one or both of the calculated metabolic rate and the measured aspects of the individual's respiration to the concurrently measured cardiac rate, or heart rate, of the individual. In addition, the present invention includes a portable calorimeter and a system that employ measurements or calculations from the calorimeter to subsequently evaluate the metabolic rate of the same individual based at least in part upon the individual's heart rate. The present invention also includes methods for evaluating the metabolic rate of an individual.

The calorimeter of the present invention is configured to receive respiratory gases exhaled by an individual. The calorimeter includes a respiratory flow detection component through which expiratory respiration of the individual passes, a mixing chamber in communication with the respiratory flow detection component, and a respiratory oxygen measurement component in communication with the mixing chamber. In use, the force of an individual's expiratory respiration drives the exhaled respiratory gases through the flow detection component, the mixing chamber, and the respiratory oxygen measurement component, each of which are positioned along a flow path through the calorimeter.

The calorimeter also includes a calibrator in communication with the respiratory oxygen measurement component. The calibrator includes a room air intake component, which, in operation, forces room air at least into the presence of the respiratory oxygen measurement component. Accordingly, room air, which is assumed to include a molecular oxygen fraction of about 20.93%, is used to calibrate the respiratory oxygen measurement component of the calorimeter at least prior to an individual's first exhalation into the calorimeter.

The respiratory flow detection component and the respiratory oxygen measurement component communicate with respective detectors, which, in turn, communicate data to a processor or to memory associated with the processor. The respiratory flow and respiratory oxygen measurements are used to determine an indicator of the metabolic rate of the individual, such as the total number of calories burned by the individual over a specific duration of time or the rate at which the individual is burning calories at a specific point in time. This indicator of metabolic rate may be stored as data in memory associated with the processor, along with corresponding data representative of one or more corresponding cardiac rates of the individual which are measured substantially concurrently with measurements taken by the calorimeter.

These metabolic rates, or the respiratory flow and respiratory oxygen data, and corresponding cardiac rate data may be communicated, or transmitted, to memory of a portable cardiac rate monitor, which is also referred to herein as a portable calorimeter for simplicity, to be subsequently used to measure the metabolic rate of the individual. The stored data may subsequently be used by the portable calorimeter to subsequently determine the metabolic rate of the individual, based upon the cardiac rate measured by the portable calorimeter, without requiring use of the calorimeter.

Other features and advantages of the present invention will become apparent to those of skill in the art through a consideration of the ensuing description, the accompanying drawings, and the appended claims.

BRIEF DESCRIPTION OF THE SEVERAL VIEWS OF THE DRAWINGS

In the drawings, which illustrate what is currently exemplary embodiments of the present invention:

FIG. 2 is a schematic representation of a portable heart rate monitor that is configured to measure the cardiac rate of an individual and to determine the metabolic rate or energy expended by the individual based upon respiratory data obtained by the calorimeter of FIG. 1 or metabolic rate data calculated by the calorimeter of FIG. 1; and FIG. 3 is a schematic representation of an exemplary use of the portable heart rate monitor shown in FIG. 2.

DETAILED DESCRIPTION OF THE INVENTION

Figure 1:
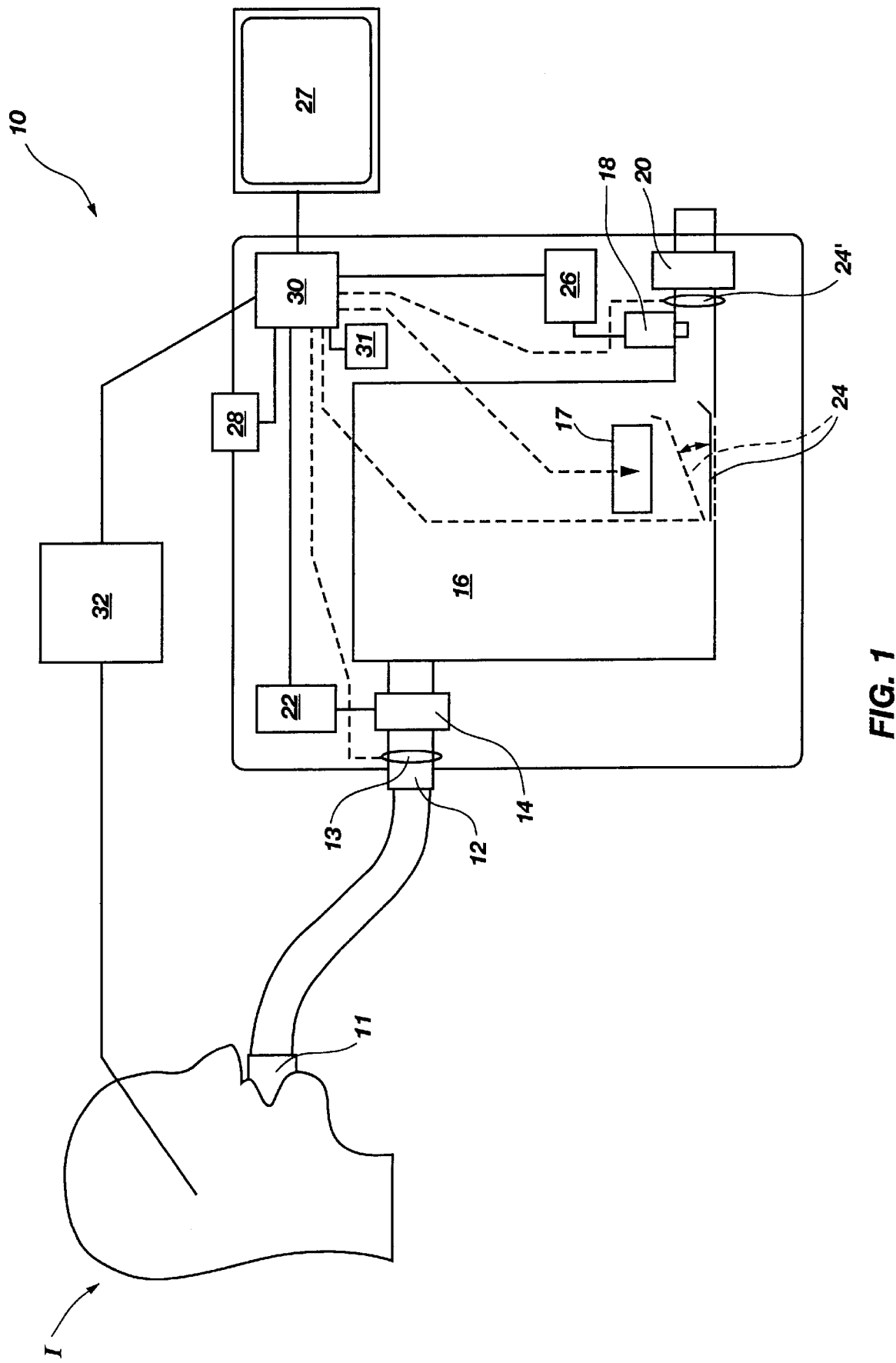
FIG. 1 is a schematic representation of a calorimeter configured to evaluate the metabolic rate of an individual by measuring various aspects of the individual's expiratory respiration, as well as a cardiac rate monitor associated with the calorimeter.

With reference to FIG. 1, a calorimeter 10 incorporating teachings of the present invention is illustrated. As shown, calorimeter 10 includes an expiratory respiration inlet 12, a respiratory flow sensor 14 in communication with expiratory respiration inlet 12, a mixing chamber 16 also in communication with expiratory respiration inlet 12, a respiratory oxygen sensor 18 in communication with mixing chamber 16, remote from expiratory respiration inlet 12, and a calibrator 20 in communication with at least respiratory oxygen sensor 18.

Expiratory respiration inlet 12 is configured to communicate with an airway of an individual I by way of an interface element 11, such as a mouthpiece or a mask, so as to direct expiratory respiration gases from the airway of individual I to respiratory flow sensor 14 and mixing chamber 16. Expiratory respiration inlet 12 may have associated therewith a one-way valve .13 configured to prevent non-expiratory gases from entering therethrough.

Respiratory flow sensor 14, which is also referred to herein as a respiratory flow measurement component, is located along a respiratory flow path through calorimeter 10 so as to receive expiratory respiration of individual I. Respiratory flow sensor 14 may comprise any known type of flow sensor, such as a mainstream or a side stream respiratory flow sensor. A flow meter 22 may communicate with respiratory flow sensor 14 so as to generate signals representative of the flow of expiratory respiration through expiratory respiration inlet 12. Flow meter 22 may communicate such signals, by way of carrier waves, to a processor 30 (e.g., a PENTIUM class microprocessor available from Intel Corp. of Santa Clara, Calif.) associated with calorimeter 10 or to memory 31 associated with processor 30.

Mixing chamber 16, which is also located along the respiratory flow path through calorimeter 10, is configured to receive and mix, or average, the gases of at least one expiratory breath of individual I. A mixing element 17, such as a fan, may be included in mixing chamber 16 so as to facilitate the mixing of gases of multiple expiratory breaths of the individual. Such mixing may, for example, cause the concentration of oxygen in the expiratory respiration of individual I contained within mixing chamber 16 to remain substantially the same, which may reduce the likelihood that the signal from oxygen sensor 18 will drift (i.e., become inaccurate) within a single breath. The operation of mixing element 17 may be controlled by processor 30.

Respiratory oxygen sensor 18, which is also referred to herein as a respiratory gas measurement component, is located directly along the flow path through calorimeter 10 and receives expiratory respiration of individual I from mixing chamber 16. Any known type of oxygen sensor, including, without limitation, a fuel cell type oxygen sensor (e.g., that available from Maxtech Inc. of Salt Lake City, Utah), a luminescence quenching type oxygen sensor, or a heated zirconia cell, may be used as respiratory oxygen sensor 18. Respiratory oxygen sensor 18 may communicate with an oxygen meter 26, or gas meter, that generates signals representative of molecular oxygen present in the expiratory respiration of the individual. Oxygen meter 26 may communicate such signals, by way of carrier waves, to processor 30 or to memory 31 associated with processor 30.

Calibrator 20 communicates with respiratory oxygen sensor 18 and is configured to facilitate the introduction of calibration gases into the presence of at least respiratory oxygen sensor 18. Calibrator 20 may comprise a fan, blower, another impeller, or another device configured to draw calibration gases, such as room air, past respiratory oxygen sensor 18. Calibrator 20 may also cause calibration gases to be introduced into mixing chamber 16. The operation of calibrator 20 may also be controlled by processor 30.

A valve 24 may be positioned on a wall of mixing chamber 16 so as to allow calibration gases that flow into calibrator 10 through or past respiratory oxygen sensor 18 to escape mixing chamber, thus preventing pressure within mixing chamber 16 from increasing to a point that may hinder the introduction of calibration gases into calorimeter 10. Conversely, as the expiratory respiration of individual I is being introduced into mixing chamber 16, valve 24 may be oriented in a closed position so as to prevent the undesired escape of respiratory gases from mixing chamber 16 and to maintain the pressure with mixing chamber 16 at a sufficient level that the force generated as individual I exhales can force the expiratory respiration of individual I through or past respiratory oxygen sensor 18. Preferably, as described hereinafter in greater detail, the positioning of valve 24 is controlled by mixing element 17 and calibrator 20.

Alternatively or in addition, another valve 24' may be disposed along the flow path between mixing chamber 16 and calibrator 20 so as to prevent room air from entering respiratory oxygen sensor 18 or mixing chamber 16 as the respiration of individual I is being evaluated. Such a valve 24' may also facilitate the introduction of calibration gases into mixing chamber 16 when the respiration of individual I is not being monitored. As shown in FIG. 1, valve 24' is a one-way valve that prevents calibration gases from entering mixing chamber while an individual I exhales into expiratory respiration inlet 12.

Valve 13 may communicate with and be under control of processor 30. Accordingly, processor 30 can open and close one-way valve 13 so as to control the introduction of expiratory respiration into calorimeter 10 through expiratory respiration inlet 12 and to prevent the escape of expiratory respiration from calorimeter 10 through expiratory respiration inlet 12. One-way valve 13 may also remain closed as room air or other another mixture of calibration gases is introduced into the presence of respiratory oxygen sensor 18.

Processor 30 may also direct the opening and closing of one or both of valves 24 and 24' so as to control the introduction of calibration gases, such as room air, into the presence of respiratory oxygen sensor 18 or into mixing chamber 16 and to facilitate the calibration of respiratory oxygen sensor 18. Processor 30 may communicate with one-way valve 13 and one or both of valves 24 and 24' in such a manner that as one of valves 13 and 24, 24' is open, the other valve 13 or 24, 24' is closed. In this manner, processor 30 may limit the introduction of only one of expiratory respiration and calibration gases into calorimeter 10.

Alternatively, mixing element 17 may be oriented toward one or both of valves 24, 24' so as to force valve 24, 24' into a closed position during operation of mixing element 17. Similarly, the fan of calibrator 20 may be oriented so as to direct a mixture of calibration gases toward valve 24, 24' in such a manner that valve 24, 24' is forced into an open position as calibration gases are introduced into calorimeter 10. Accordingly, processor 30 may indirectly control the opening and closing of valve 24, 24' by controlling the operation of one or both of mixing element 17 and calibrator 20.

Processor 30 may communicate with and control the operation of calibrator 20. Accordingly, processor 30 may coordinate the introduction of calibration gases into calorimeter 10 with the introduction of the expiratory respiration of an individual into calorimeter 10 in such a manner that both of these operations do not occur at the same time.

Calorimeter 10 may also include one or more additional elements, including, without limitation, an output device 27, a humidity monitor 28, and a heart rate monitor 32.

A heart rate monitor 32, or cardiac rate monitor, may be associated with calorimeter 10 so as to evaluate the heart rate, or cardiac rate, of individual I as individual I exhales into expiratory respiration inlet 12 of calorimeter 10. Preferably, heart rate monitor 32 communicates with processor 30 so that processor 30 may correlate the expiratory respiration and expiratory gases of individual I with the heart rate of individual I.

Humidity sensor 28 may be of a known type and is preferably configured to measure an amount, or percent, of water vapor (i.e., humidity) present in the ambient gases (e.g., room air) being inhaled by individual I. Humidity sensor 28 may communicate signals representative of the amount of ambient water vapor. to processor 30 or to memory 31 associated with processor 30.

Output device 27 may comprise a visual display (e.g., a liquid crystal display (LCD), a field emission display (FED), a computer monitor, etc.), an audio output device (e.g., an audible alarm), or a combination thereof. Output device 27 may communicate with processor 30 so as to display data representative of the respiratory flow or gas content of the expiratory respiration of individual I or of the cardiac rate of individual 1, as well as data calculated by processor 30 based on these measurements. Output device 27 may also display data or information regarding the communication of information from processor 30 to peripheral apparatus, such as the portable cardiac rate monitor 40 described hereinafter with reference to FIG. 2.

With continued reference to FIG. 1, an exemplary method for calibrating respiratory oxygen sensor 18 of calorimeter 10 in accordance teachings of the present invention includes opening valve 24 and actuating calibrator 20 so as force room air or another mixture of calibration gases through or past respiratory oxygen sensor 18. When actuated, calibrator 20 may also force room air into mixing chamber 16 so as to prevent as residual gases within mixing chamber 16 from affecting the calibration of respiratory oxygen sensor 18. The flow or calibration gases into calorimeter 10 may be verified as respiratory flow sensor 14 detects gas flow. The amount of calibration gas flow measured by flow sensor 14 is communicated, via flow meter 22, to processor 30, which transmits signals to output device 27 so as to indicate whether or not the flow of calibration gases through calorimeter 10 is sufficient for calibration.

As room air flows through or past oxygen sensor 18, oxygen meter 26, which communicates with oxygen sensor 18, generates signals representative of an amount of oxygen present in the room air. These signals may be communicated, as known in the art, such as by carrier waves, to processor 30. Processor 30 then calibrates these signals so that they are representative of the known or assumed amount of oxygen present in the room air. In so calibrating the signals from oxygen meter 26, adjustments may be made, as known in the art, for the amount of water vapor, or humidity, present in the room air, as measured by a humidity sensor 28 associated with calorimeter 10 and processor 30. For example, processor 30 may assume that the amount of oxygen present in the room air is equal to about 20.93%. The room air may have a humidity of about 25%. The intensity of the signal generated and transmitted by oxygen meter 26 is then calibrated to be equal to the known or assumed amount of oxygen in the room air at a 25% humidity level. This calibrated signal intensity may then be used as a reference point in determining the amount of oxygen present in the expiratory respiration of an individual I. Calibration of respiratory oxygen sensor 18 is preferably effected immediately before use of calorimeter 10.

Calorimeter 10 may be used to monitor the expiratory respiration of individual I over a substantially steady level of physical exertion, but is preferably used to monitor the expiratory respiration and cardiac rate of individual I over a range of physical exertion. For example, a so-called "ramp protocol" or "step protocol" may be used to measure the amounts of oxygen consumption of individual I at rest and a increasing levels of physical exertion.

Still referring to FIG. 1, in use of calorimeter 10 to determine the metabolic rate of individual I, individual I exhales one or more breaths into interface element 11 and expiratory respiration inlet 12 with valve 13 in an open position and valve 24 in a closed position. The flow rate of the exhalation of individual I is monitored by respiratory flow sensor 14 and measured by flow meter 22. Signals representative of the flow of the exhalation of individual I may be transmitted, by way of carrier waves, to processor 30 or to memory 31 associated therewith.

The expiratory respiration of individual I also enters mixing chamber 16, where mixing element 17 may mix the gases of one or multiple expiratory breaths so as to equilibrate concentrations of the expiratory gases throughout mixing chamber 16. The pressure created within calorimeter 10 by the exhalation of individual I forces some of the expiratory gases within mixing chamber 16 out of mixing chamber 16 and through or past respiratory oxygen sensor 18. Oxygen sensor 18 monitors oxygen in the expiratory respiration of individual I, while oxygen meter 26 communicates with oxygen sensor 18 so as to measure the amount, or fraction, of oxygen in the expiratory respiration of individual I. Oxygen meter 26 may transmit signals, or carrier waves, representative of the amount of oxygen in the expiratory respiration of individual I to processor 30 or to memory 31 associated therewith, as known the art.

Once data representative of the amount of oxygen present in the expiratory respiration of an individual and data representative of the individual's respiratory flow rate have been transmitted to processor 30, processor 30 may calculate a metabolic rate of the individual or a rate at which the individual burns calories.

Processor 30 may calculate the metabolic rate of individual I by known techniques. By way of example and not to limit the scope of the present invention, the amount of oxygen consumed by individual I may be calculated by use of the following equation:

$$VO_2 = Vi \times FiO_2 - Ve \times FeO_2,$$

where $VO_2$ is the volume of oxygen consumed, or metabolized, by individual I; Vi is the volume of gas inspired by individual I; $FiO_2$ is the fraction, or percent, of oxygen in the inspired gas; Ve is the volume of gases exhaled by individual I; and $FeO_2$ is the fraction, or percent, of oxygen in the expiratory respiration of individual I.

Ve and $FeO_2$ may be determined based on direct measurements. For example, respiratory flow sensor 14 and flow meter 22 may be used to measure the flow of expiratory respiration of individual I, which may then be used to determine Ve, as known in the art. Respiratory oxygen sensor 18 and oxygen meter 26 may be used to directly measure $FeO_2$ over the course of one or more expiratory breaths of individual I.

Vi may be estimated by use of the Haldane transform, as known in the art, or measured directly by use of a respiratory flow sensor in communication with the airway of individual I. $FiO_2$ may be an assumed value, such as 20.93% for dry gas in room air. Alternatively, $FiO_2$ may be directly measured by use of an oxygen sensor and meter.

The effects of water vapor present in the inhaled air or gases on the $FeO_2$ or $FiO_2$ measurements may be accounted for as known in the art.

As an alternative, a respiratory carbon dioxide sensor of a known type may be used in place of respiratory oxygen sensor 18 as the respiratory gas measurement component of calorimeter 10. As with oxygen sensor 18, measurements obtained by a carbon dioxide sensor may be communicated to a gas meter, such as a carbon dioxide sensor which, in turn, communicates signals representative of the amount of carbon dioxide in the expiratory respiration of individual I to processor 30. When a carbon dioxide sensor is used, $VCO_2$ may be determined and $VO_2$ calculated based on an assumed or estimated respiratory quotient (RQ) of individual I and the $VCO_2$ measurement, as follows:

$$RQ = VCO_2/VO_2,$$

where RQ may be assumed to be in the range of about 0.7 to 1.0 and, more particularly, about 0.8 to 0.9 or 0.86.

As a known, fixed amount of oxygen is required for the body of an individual I to metabolize one calorie, once the $VO_2$ of individual I has been determined, the total amount of energy, in calories, expended (or the number of calories metabolized) by individual I over a known period of time or the rate at which individual I is expending energy (or metabolizing calories) at a specific point in time may be determined.

Processor 30 may then correlate the calculated metabolic rate or rates of individual I with one or more levels of physical exertion, which may, for example, be indicated by the one or more measured cardiac rates of individual I.

Referring now to FIG. 2, a portable calorimeter 40 of the present invention, which is useful in systems and methods incorporating teachings of the present invention, includes a processor 42, memory 43 associated with processor 42, a cardiac rate monitor 44 in communication with processor 42, an output element 46 in communication with processor 42, and a communication port 48, also in communication with processor 42.

A cardiac rate monitor 44 of a known type is configured to sense the pulse of an individual I when positioned in proximity to a location on individual I, such as the wrist or neck, where the pulse or cardiac rate of individual I can be accurately measured.

As shown, output element 46 includes a display screen of a known type, such a light emitting diode (LED) or a field emission display (FED), through which processor 42 communicates data or information to individual I derived from the measured cardiac rate of individual I. Alternatively, output element 46 may comprise another type of visual display element, an audio alarm or other audio output device, or any other known type of output element that would be useful for communicating metabolic rate information to individual I. As another alternative, portable calorimeter 40 may include a. combination of different types of output elements 46.

Communication port 48 is configured to facilitate communication between processor 42 of portable calorimeter 40 and processor 30 of calorimeter 10. Communication port 48 may comprise any known communication element, such as an infrared (IR) port, a universal serial bus (USB) port, or any other suitable type of input/output (I/O) port. In any event, the transmittal of data signals, or carrier waves, to processor 42 through communication port 48 may be controlled by one or both of processor 42 of portable calorimeter 40 and a processor of a calorimeter that has been used to measure the respiration of individual I and relate measured respiratory data or metabolic rate data calculated from the measured respiratory data of individual I to the cardiac rate of individual I (e.g., processor 30 of calorimeter 10). In particular, data representative of the metabolic rate of individual I, or of the respiratory flow and oxygen fraction of the expiratory respiration of individual I, correlated with one or more cardiac rates of the individual may be communicated from memory 31 associated with processor 30 to memory 43 associated with processor 42.

Turning now to FIG. 3, and with continued reference to FIG. 2, an example of the use of portable calorimeter 40 is illustrated. Portable calorimeter 40 is worn by individual I in such a manner that cardiac rate monitor 44 is in proximity to a location on individual I where the cardiac rate, or pulse, of individual I can be accurately monitored and measured. In use, cardiac rate monitor 44 communicates signals, or carrier waves, representative of the cardiac rate of individual I to processor 42.

Upon receiving signals representative of the cardiac rate of individual I, processor 42 determines a metabolic rate of individual I based on the measured cardiac rate and metabolic rate data of individual I stored in memory 43 associated with processor 42. Alternatively, processor 42 may calculate the metabolic rate of individual I based on respiratory flow and oxygen fraction data of individual I stored in memory 43 and that correspond to the cardiac rate of individual I measured by cardiac rate monitor 44 of portable calorimeter 40.

The calculated metabolic rate of individual I may then be communicated from processor 42 to output element 46, as known in the art. Accordingly, if output element 46 is a display screen, various data representative of the metabolic rate of individual I may be shown in a numerical or graphic format. For example, the total number of calories burned by individual I over a specified duration of time may be displayed, the rate at which individual I is currently burning calories may be displayed, or other data representative of the metabolic rate of individual I may be displayed. In addition, other information, such as the current time, the elapsed duration of the activity of individual I, and the current or average cardiac rate of individual I, may be shown on the display screen of output element 46.

The metabolic rate of individual I may be periodically reevaluated by calorimeter 10 and the data stored in memory 43 of portable calorimeter 40 replaced or supplemented so as to account for changes in the metabolism of individual I that may occur as individual I ages, with changes in the fitness of individual I, with changes in the physical health of individual I, or due to other causes.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A calorimeter, comprising:

an inlet configured to communicate with an airway of an individual to receive expiratory gases from the individual;

a respiratory flow detection component in communication with said inlet;

a mixing chamber in communication with said inlet to receive at least one expiratory breath from the individual and average the respiratory gases of said at least one expiratory breath;

a respiratory gas measurement component in communication with said mixing chamber and downstream therefrom to receive expiratory respiration from the individual under pressure of the individual's expiratory breaths;

an outlet located so as to receive gas from said respiratory gas measurement component and to expel the gas from the calorimeter; and a calibrator in communication with at least said respiratory gas measurement component and said outlet and positioned so as to draw calibration gas into the calorimeter through said outlet to a location for detection by at least said respiratory gas measurement component.

2. The calorimeter of claim 1, wherein said respiratory gas measurement component comprises an oxygen sensor.

3. The calorimeter of claim 1, further comprising:

a flow meter in communication with said respiratory flow detection component; and a gas meter in communication with said respiratory gas measurement component.

4. The calorimeter of claim 3, wherein said gas meter comprises an oxygen meter.

5. The calorimeter of claim 3, further comprising a processor in communication with said flow sensor and said gas sensor.

6. The calorimeter of claim 5, wherein said processor also communicates with a cardiac rate monitor.

7. The calorimeter of claim 1, wherein said inlet includes a 1-way valve positioned so as to control the movement of gas through said inlet.

8. The calorimeter of claim 1, wherein said mixing chamber comprises a valve positioned so as to control pressure within said mixing chamber.

9. The calorimeter of claim 8, wherein said mixing chamber comprises a mixing element, said mixing element and a fan of said calibrator oriented so as to control positioning of said valve.

10. The calorimeter of claim 1, further comprising a valve configured to control the flow of calibration gas into said location for detection by at least said respiratory gas measurement component.

11. The calorimeter of claim 10, wherein said valve is positionable to prevent exposure of said respiratory gas measurement component to room air as the individual breathes into said inlet.

12. A system for measuring a metabolic rate of an individual, comprising:
  a calorimeter including:
  an inlet configured to receive expiratory respiration from the individual;
  a respiratory flow sensor in communication with said inlet;
  a mixing chamber in communication with said inlet to receive at least one expiratory breath from the individual; and
  a gas sensor in communication with said mixing chamber;
  a flow meter in communication with said respiratory flow sensor;
  a gas meter in communication with said gas sensor;
  a cardiac rate monitor;
  a processor in communication with said flow meter, said gas meter, and said cardiac rate monitor; and
  a portable calorimeter configured to communicate with said processor so as to receive data therefrom.

13. The system of claim 12, wherein said calorimeter further includes a calibrator configured to introduce room air into the presence of said gas sensor.

14. The system of claim 12, wherein said processor is configured to determine the metabolic rate based on flow data generated by said flow meter and respiratory gas data generated by said gas meter.

15. The system of claim 14, wherein said portable calorimeter is configured to store data representative of the metabolic rate of the individual and to employ such stored data along with measured cardiac rate data to determine a metabolic rate of the individual without again requiring use of said calorimeter.

16. The system of claim 12, wherein:
  said gas sensor comprises at least one of an oxygen sensor and a carbon dioxide sensor; and
  said gas meter comprises at least one of an oxygen meter and a carbon dioxide meter.

17. A method for measuring a metabolic rate of an individual, comprising:
  evaluating expiratory respiration of the individual to determine an oxygen consumption of the individual;
  measuring a cardiac rate of the individual substantially concurrently with said evaluating;
  transmitting data representative of said oxygen consumption and said cardiac rate to a portable calorimeter;
  measuring a cardiac rate of the individual following said transmitting; and
  calculating the metabolic rate of the individual based on said transmitted data and said cardiac rate measured by said portable calorimeter.

18. The method of claim 17, further comprising disassociating said portable calorimeter from said processor.

19. A portable calorimeter configured to be worn by an individual, comprising:
  a processor;
  a cardiac rate monitor in communication with said processor, said cardiac rate monitor being configured to communicate signals representative of a cardiac rate of the individual to said processor, said processor being configured to determine a metabolic rate of the individual based on previously obtained respiratory or metabolic rate data of the individual; and
  an output element in communication with said processor and being configured to communicate information representative of at least the metabolic rate of the individual.

20. The portable calorimeter of claim 19, wherein said output element is configured to communicate at least one of an amount of energy expended by the individual over a period of time and a rate at which the individual is expending energy.

21. A calorimeter, comprising:
  a flow path in communication with an airway of an individual;
  a respiratory gas measurement component positioned along said flow path so as to receive gases exhaled by the individual without use of a valve or pump; and
  a calibrator in communication with said flow path and configured to cause at least one calibration gas to flow through said flow path in an opposite direction from that in which gases exhaled by the individual flow so as to expose said respiratory gas measurement component to said at least one calibration gas.

22. The calorimeter of claim 21, wherein said calibrator comprises a fan.

* * * * *

UNITED STATES PATENT AND TRADEMARK OFFICE
CERTIFICATE OF CORRECTION

PATENT NO. : 6,475,158 B1
DATED : November 5, 2002
INVENTOR(S) : Joseph A. Orr, Scott A. Kofoed and Kevin Durst It is certified that error appears in the above-identified patent and that said Letters Patent is hereby corrected as shown below:

Column 1,
Line 53, before "individual" change "the," to -- the --

Column 2,
Line 3, change "Merialäinen" to -- Meriläinen --

Column 4,
Line 50, change ".13" to -- 13 --
Line 55, change "10so" to -- 10 so --

Column 5,
Line 38, change "calibrator 10" to -- calorimeter 10 --

Column 6,
Line 53, delete the period after "vapor"
Line 62, change "individual 1" to -- individual I --
Line 66, after "portable" change "cardiac rate monitor 4O" to -- calorimeter 40 --

Column 7,
Line 3, after "accordance" and before "teachings" insert -- with --
Line 47, before "increasing" change "a" to -- at --

Signed and Sealed this

First Day of July, 2003

JAMES E. ROGAN
*Director of the United States Patent and Trademark Office*